United States Patent [19]
Frigg

[11] Patent Number: 4,978,349
[45] Date of Patent: Dec. 18, 1990

[54] FIXATION PLATE
[75] Inventor: Robert Frigg, Wayne, Pa.
[73] Assignee: Synthes (U.S.A.), Paoli, Pa.
[21] Appl. No.: 388,848
[22] Filed: Aug. 3, 1989
[51] Int. Cl.⁵ .............................................. A61F 5/04
[52] U.S. Cl. ........................................ 606/67; 606/62
[58] Field of Search ........ 128/92 YZ, 92 YK, 92 YY, 128/92 YP; 606/67, 62, 68, 72, 63-66

[56] References Cited
U.S. PATENT DOCUMENTS

| | | | |
|---|---|---|---|
| 3,025,853 | 3/1962 | Mason | 606/67 |
| 4,103,683 | 8/1978 | Neufeld | 606/67 |
| 4,341,206 | 7/1982 | Perrett et al. | |
| 4,628,920 | 12/1986 | Mathys et al. | 606/62 |
| 4,697,585 | 10/1987 | Williams | 606/64 |
| 4,733,654 | 3/1988 | Marino | 606/64 |
| 4,827,917 | 5/1989 | Brumfield | 606/64 |
| 4,915,092 | 4/1990 | Firica et al. | 606/67 |

FOREIGN PATENT DOCUMENTS
0257118 8/1986 European Pat. Off. .

OTHER PUBLICATIONS
"Gamma Locking Nail" Brochure, Howmedica, undated.
"Russell-Taylor Reconstruction Nail" Brochure, Campbell Clinic, exhibit presented Feb. 9-14, 1989.

Primary Examiner—David J. Isabella
Assistant Examiner—David H. Willse
Attorney, Agent, or Firm—Davis Hoxie Faithfull & Hapgood

[57] ABSTRACT

An osteosynthetic fixation plate comprising a retaining plate and a helically twisted blade extending therefrom, for use in treatment of fractures to the neck of the femur.

8 Claims, 4 Drawing Sheets

FIXATION PLATE

FIELD OF THE INVENTION

This invention relates to a fixation device for use in osteosynthesis and specifically a fixation plate for treatment of fractures of the femur which extend into the neck of the femur.

BACKGROUND OF THE INVENTION

Fractures of the femur which extend into the neck of the bone are generally more difficult to treat than fractures restricted to the shaft of the femur. Various osteosynthetic devices have been used in the treatment of these difficult fractures.

In one class of devices an intramedullary nail having transverse holes at or near its head is inserted into the femur and then one or more screws are inserted angularly across the head of the intramedullary nail. Such a nail is shown, for example in EPO patent application Ser. No. 0,257,118 published Mar. 2, 1988. A similar device is the "Gamma" locking nail, sold by Howmedica. Another design is the Russell-Taylor Reconstruction nail. All such prior devices have one deficiency or another. Some require extremely large or heavy screws; or where small transverse screws are employed the device does not provide adequate support. There is a need, therefore, for a device for reduction and stabilization of this type of fracture of the femur which is strong, light and relatively simple to implant.

SUMMARY OF THE INVENTION

The fixation device of the invention overcomes the disadvantages of the prior art treatments of femur fractures which extend into the neck of the femur. In a principal aspect, it comprises a fixation plate which includes an outer retaining plate which can be attached, as by screws, to the shank of the femur and a blade extending from the retaining plate and designed to extend into the neck of the femur. The blade is twisted helically about 90° and is adapted to pass through a slot in an intramedullary nail which has been driven into the shank of the femur. The retaining plate has one or more screw holes to accommodate screws for fastening the plate to the nail.

In a second aspect, the invention includes an assembly for fixation of fractures of the femur which extend into the neck of the femur comprising a fixation plate as described and an intramedullary nail having a slot designed to receive the blade of the fixation plate. In another aspect, the invention comprises a method of stabilizing fractures of the femur which extend into the neck of the femur which includes inserting an intramedullary nail, as described, into the medulla of the femur and then positioning a fixation plate, as described, with its blade extending through the slot in the nail.

DESCRIPTION OF THE DRAWINGS

The invention will be further described with reference to the accompanying drawings, wherein.

DETAILED DESCRIPTION

Figure 3:
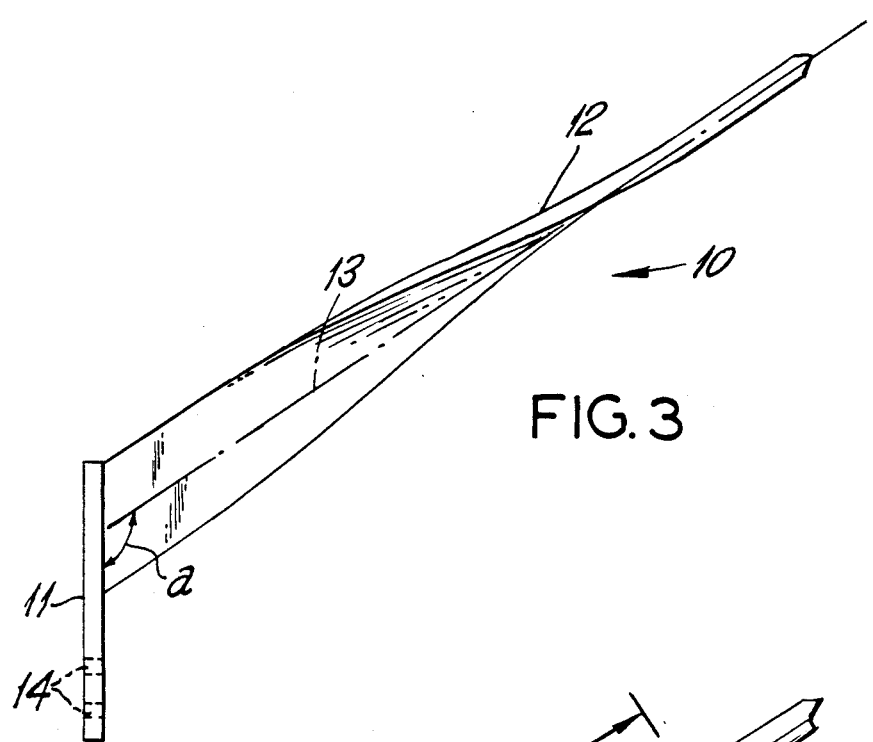
FIG. 3 is a view in side elevation of a fixation plate according to the invention.

Referring first to FIG. 3, a fixation plate 10 according to the invention comprises a retaining plate 11 which is adapted to lie along the shaft of the femur and a blade 12 which extends transversely to the plane of plate 11. The axis 13 of the blade forms an angle a with the plane of plate 11 which may vary according to the patient, but which will in general be between about 90° and about 150°.

As shown in FIG. 3, the blade is helically twisted around its axis, the total angular displacement being about 90°.

The retaining plate 11 may be furnished with one or more screw holes 14 for fixing the plate to the shaft of the femur.

Figure 4:
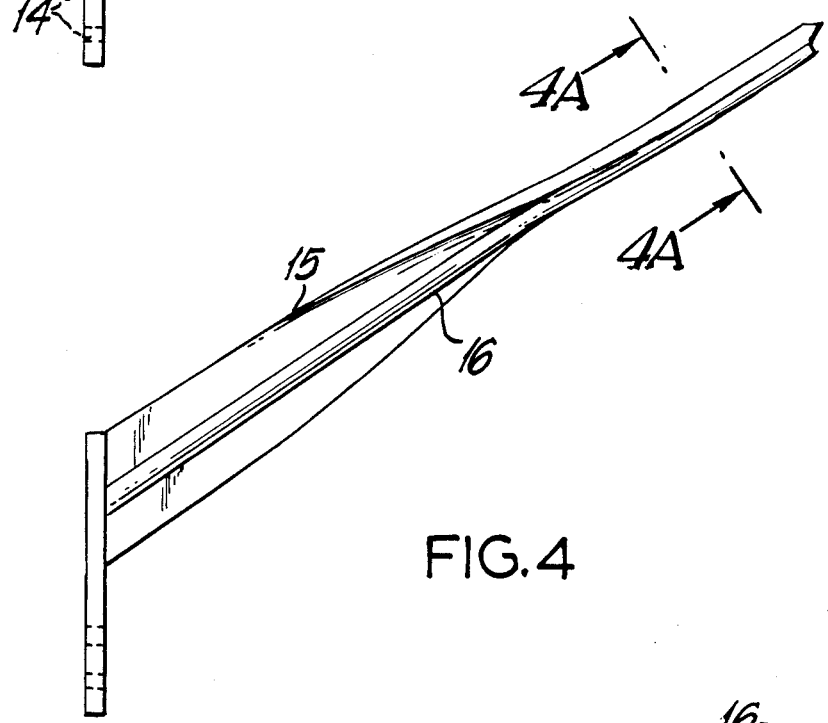
FIG. 4 is a view in side elevation of a modified fixation plate according to the invention.
Figure 4A:
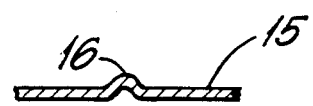
FIG. 4A is a cross sectional view, showing the section A—A of FIG. 4.

A modified version of the fixation plate is shown in FIGS. 4 and 4A. Referring to these figures, the blade 15 of the fixation plate may be provided with a cannula 16 for receiving a Kirschner wire or the like to facilitate insertion of the blade into the bone, in the manner described below.

Figure 1:
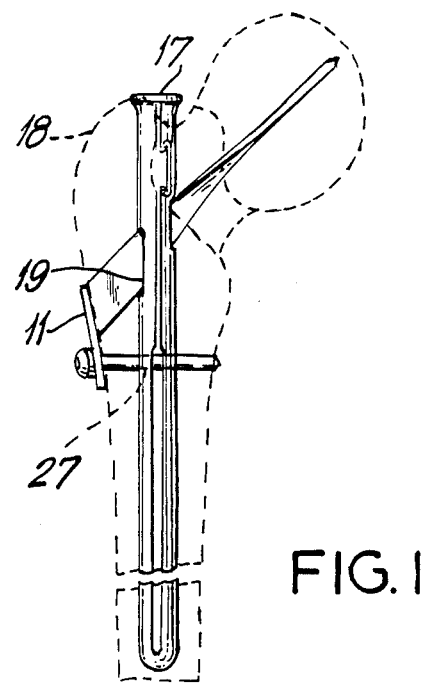
FIG. 1 is a schematic view showing an assembly including a fixation plate and an intramedullary nail according to the invention implanted in a femur.
Figure 2:
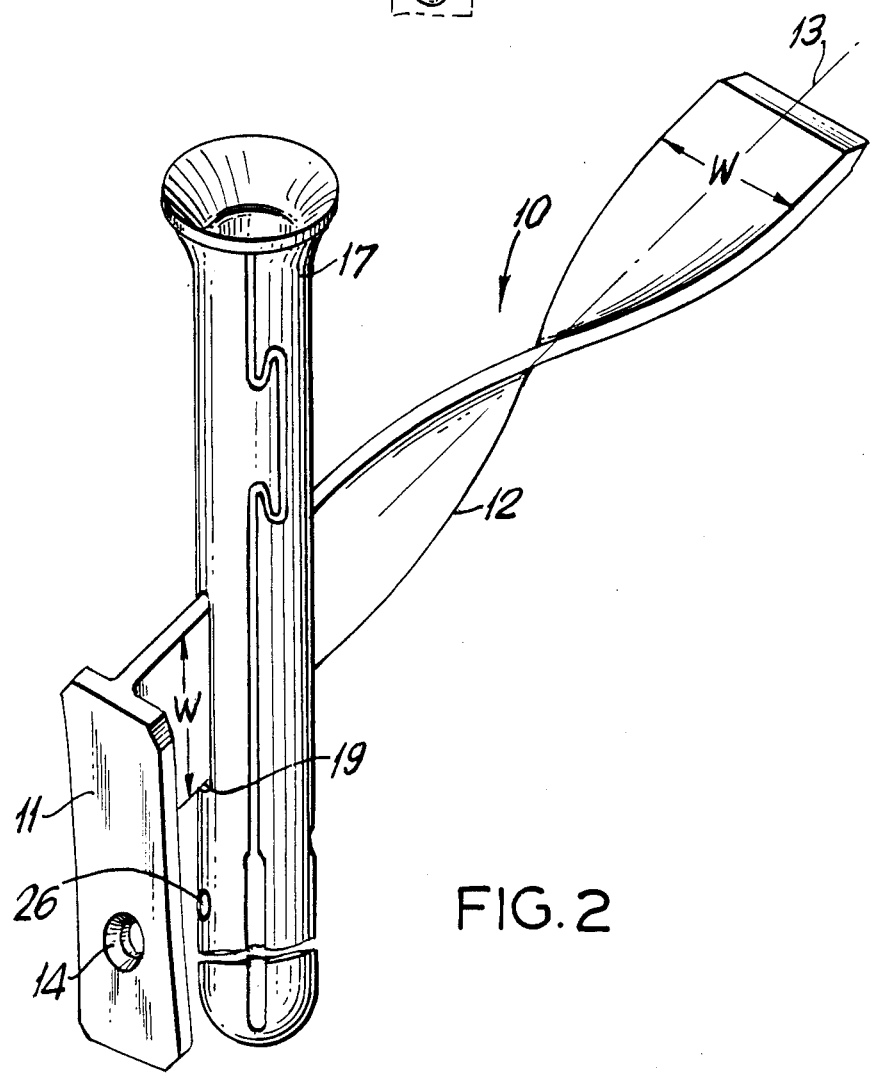
FIG. 2 is a more detailed, partially fragmentary, schematic view showing a fixation plate according to the invention inserted in an intramedullary nail.

As indicated previously, the fixation plate of the invention is used in conjunction with an intramedullary nail. The combination is shown in FIGS. 1 and 2. Referring to FIG. 1, an intramedullary nail 17 is shown positioned in the medulla of a femur 18. The nail may be of any suitable design, although it is preferred to use a nail of the type shown and described in U.S. Pat. No. 4,628,920. The nail is provided with slots such as 19 to accommodate the blade 12 of the fixation plate 10 and one or more through holes 26 to accommodate one or more retaining screws inserted through screw hole 14 in retaining plate 11. Additional screw holes (not shown) may be provided to permit transverse retaining screws or bolts (not shown) to be inserted at the distal end of the nail.

A method of using an assembly according to the invention is shown in FIGS. 5 to 8.

Figure 5:
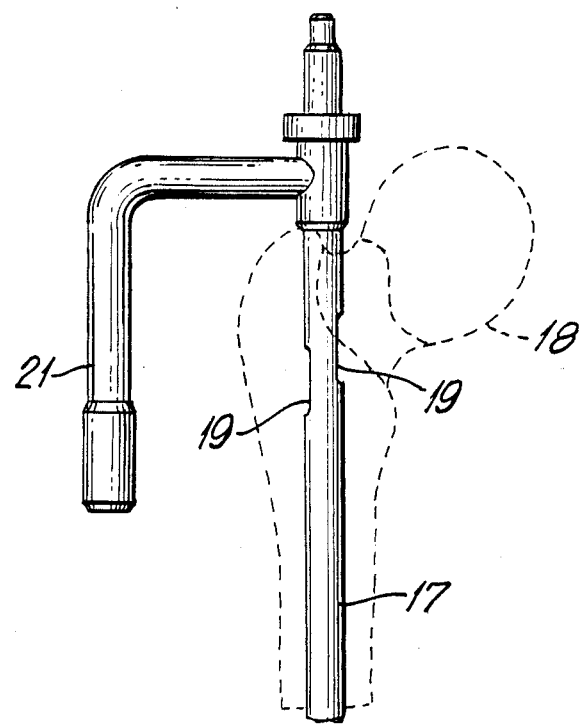
FIG. 5 is a schematic view showing insertion of an intramedullary nail into a femur in a procedure according to the invention.
Figure 6:
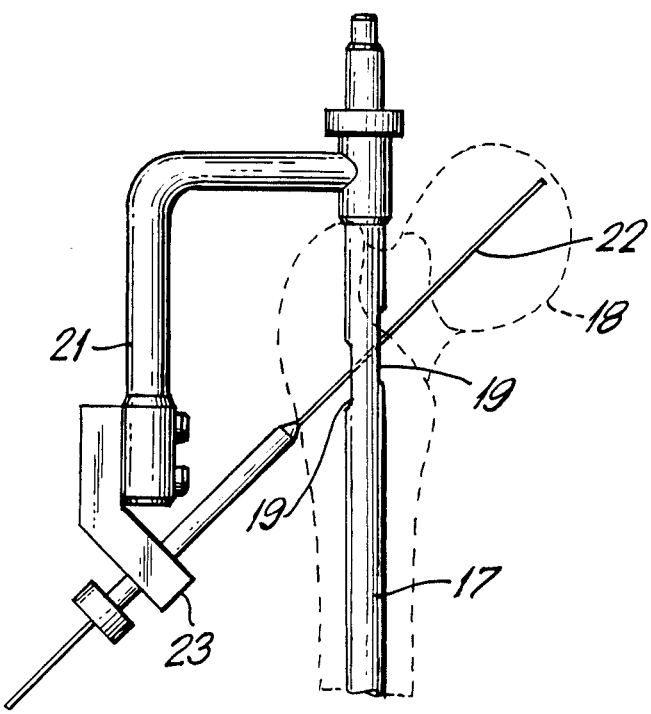
FIG. 6 is a schematic view showing insertion of a guide wire such as a Kirschner wire in a procedure according to the invention.

In FIG. 5, an intramedullary nail 17 having the structure shown in FIGS. 1 and 2 has been inserted into the shaft of a femur 18, in conventional manner. Attached to the intramedullary nail is an insertion handle 21, a standard fixture used to insert intramedullary nails. Following emplacement of the nail, as shown in FIG. 6, a Kirschner guide wire 22 may be inserted through the area of the fractures in the neck of the femur, passing through slot 19 in the nail. The Kirschner wire may be installed in a conventional manner using an alignment device 23, attached to the insertion handle 21 to ensure that it is placed at the proper angle. The Kirschner wire extends from the exterior of the femur through the bone across the fracture or fractures.

Figure 7:
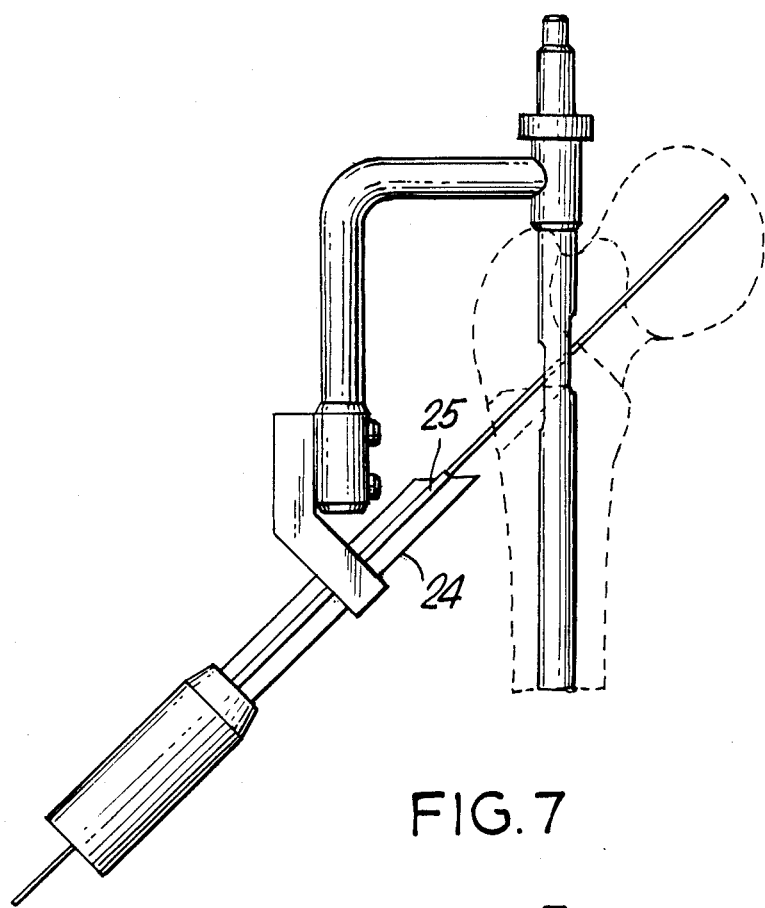
FIG. 7 is a schematic view showing use of a chisel in a procedure according to the invention.

As shown in FIG. 7 the Kirschner wire 22 may then be used to guide the insertion of a chisel 24 into the bone at the correct angle to cut a hole in the side of the bone. The chisel may be cannulated, as at 25, to ensure alignment with the Kirschner wire.

Figure 8:
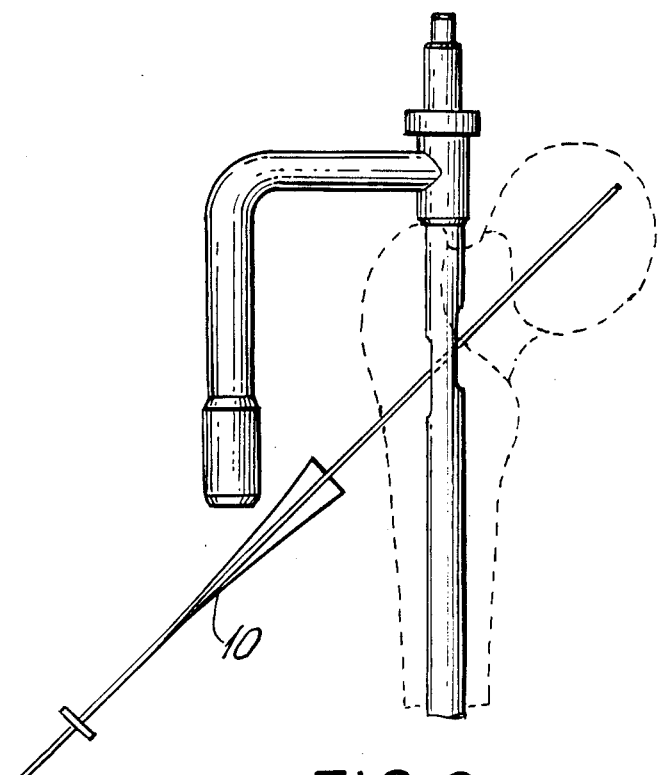
FIG. 8 is a schematic view showing insertion of a fixation plate in a procedure according to the invention.

FIG. 8 shows the fixation plate 10 of the invention about to be inserted into the fractured femur. If the blade is cannulated, as shown in FIGS. 4 and 4A, the plate's cannula is slid over the Kirschner wire to ensure insertion of the nail at the correct angle. It is not necessary, however, to have such a cannula on the plate.

Referring back to FIG. 1, the plate has been inserted and the outer plate portion lies against the exterior of the femur. A screw 27 is inserted through the screw hole 14 in the retaining plate, into the bone and through screw hole 26 in the intramedullary nail 17.

Referring to FIG. 2, when the blade is inserted in the intramedullary nail its major dimension, W, transverse to its axis 13, of the portion of the blade in and near the slot is parallel to the axis of the nail 17 and, in general, parallel to the axis of the femur into which the nail 17 is inserted. Thus the major bending stress, which will occur at the end of the blade nearest the retaining plate 11, will be borne by the major dimension of the blade. On the other hand, at the outer end of the blade, its major dimension, W, will be transverse to the axis of the nail 17 and to the axis of the femur in which it is inserted. Thus the blade will give maximum support where it is needed.

The blade portion of the plate has a large surface area, yet the plate is less bulky than prior art devices. It is able to support soft bone structure.

The plate of the invention is useful for treatment of intertrocharic fractures and fractures of the neck of the femur. It may also be used to treat brittle bones, such as those caused by osteoporosis. Since smaller, lighter nails may be used with this plate, there is less damage to the rest of the bone. It is easier to remove than plates of the prior art. Furthermore, when this plate is used, it is often unnecessary to ream out as much of the bone as is the case with the prior art devices. The same plate may be used for treatment of fractures of either the left or right femur.

What I claim is:

1. An assembly for use in osteosynthesis, said assembly comprising an intramedullary nail for insertion into the medulla of a femur and a fixation device, said fixation device having a retaining plate for positioning along the outside surface of the shank of the femur and a helically twisted blade extending from said plate for insertion into the head of the femur, and said nail having a through slot to receive and support the blade of said fixation device, while permitting movement of said blade relative to said nail, said nail and the retaining plate of said fixation device having cooperating apertures for receiving retaining means extending through the aperture of said plate, through the bone and into the aperture of said nail.

2. An assembly according to claim 1 wherein the blade is twisted approximately 90°.

3. An assembly according to claim 2 wherein the blade is twisted continuously.

4. An assembly according to claim 1 wherein the blade has a longitudinal axis which forms an angle in the range of 90° to 150° with the plane of said plate.

5. An assembly according to claim 1 wherein the blade has a cannula for receiving a guide wire.

6. An assembly according to claim 1 wherein that portion of the blade nearest the retaining plate is orthogonal to said plate.

7. An assembly according to claim 1 wherein when said blade is positioned in the slot of said nail, the portion of the blade in the slot has its major dimension generally parallel to the longitudinal axis of said nail, and the portion of the blade most remote from the retaining plate has its major dimension generally transverse to the longitudinal axis of said nail.

8. A method of treating a fracture of the femur extending into the neck of the femur which comprises inserting an intramedullary nail having a longitudinal through slot into the medulla of the femur, positioning a fixation device having a retaining plate and a transverse helically twisted blade so that the retaining plate lies along the outside surface of the lateral shank of the femur and the blade extends through the slot in the nail into the head of the femur, and securing the retaining plate both to the lateral shank of the femur and to the nail.

* * * * *

UNITED STATES PATENT AND TRADEMARK OFFICE
CERTIFICATE OF CORRECTION

PATENT NO. : 4,978,349

DATED : December 18, 1990

INVENTOR(S) : Robert Frigg

It is certified that error appears in the above-identified patent and that said Letters Patent is hereby corrected as shown below:

Abstract:

Line 3, after "fractures" change "to" to ---in---.

Col. 2, line 23 change "a" to "$\underline{a}$".

Col. 4, line 43, after "the" insert ---lateral---.

Col. 4, line 44, after "the" delete "lateral".

Signed and Sealed this

Twenty-fourth Day of November, 1992

Attest:

DOUGLAS B. COMER

*Attesting Officer*      Acting Commissioner of Patents and Trademarks